US006606397B1

United States Patent
Yamamoto

(10) Patent No.: US 6,606,397 B1
(45) Date of Patent: Aug. 12, 2003

(54) FACE IMAGE PROCESSING APPARATUS FOR EXTRACTION OF AN EYE IMAGE BASED ON THE POSITION OF THE NARIS

(75) Inventor: Takayuki Yamamoto, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/432,594

(22) Filed: Nov. 12, 1999

(30) Foreign Application Priority Data

May 25, 1999 (JP) .......................................... 11-145097

(51) Int. Cl.⁷ .............................. A61B 3/10; G06K 9/00
(52) U.S. Cl. ....................... 382/117; 382/118; 382/291; 340/575; 340/576; 351/205
(58) Field of Search .............................. 382/117, 118, 382/104, 291; 351/205; 340/573.1, 575, 576

(56) References Cited

U.S. PATENT DOCUMENTS

| | | | | |
|---|---|---|---|---|
| 5,805,720 A | * | 9/1998 | Suenaga et al. | 340/575 |
| 5,878,156 A | * | 3/1999 | Okumura | 340/575 |
| 6,055,323 A | * | 4/2000 | Okumura | 382/115 |
| 6,130,617 A | * | 10/2000 | Yeo | 340/575 |
| 6,292,575 B1 | * | 9/2001 | Bortolussi et al. | 382/118 |

FOREIGN PATENT DOCUMENTS

| JP | 08-175218 | 7/1996 | ........... B60K/28/06 |
|---|---|---|---|
| JP | 08-300978 | 11/1996 | ........... B60K/28/06 |

OTHER PUBLICATIONS

Japanese Publication 10–307923, Makahito et al., Face Parts Extraction Device and Face Direction Device, Nov. 1998.*
Japanese Publication 06–227278, Masayuki et al., Driver Condition Sensing Device, Aug. 1994.*

* cited by examiner

Primary Examiner—Bhavesh M. Mehta
Assistant Examiner—Christopher Sukhaphadhana
(74) Attorney, Agent, or Firm—Sughrue Mion, PLLC

(57) ABSTRACT

The present invention provides a face image processing apparatus capable of preventing the error extraction of the eye when extracted, and improving reliability in the open/close detection through a two-dimensional feature of the eye area. This face image processing apparatus comprises: a camera (2) for inputting a face image of a person to be detected (1); a multi-valued image memory (3) for temporarily storing the light and shade image obtained by the camera (2); binarization means (4) for binarizing the light and shade image outputted from the multi-valued image memory (3); a binary image memory (5) for temporarily storing the binary image obtained by the binarization means (4); feature extraction means (6A) for extracting a naris binary area from the binary image outputted from the binary image memory (5), and for extracting an eye binary area from the binary image outputted from the binary image memory (5) using the naris binary area as reference; and open/close detection means (7A) for detecting the opening/closing states of the eye based on the shape feature of the eye binary area.

2 Claims, 13 Drawing Sheets

■ BINARY PIXEL=1

☐ BINARY PIXEL=0

☐ BINARY PIXEL WITH MINIMUM DEVIATION OF NARIS=1

WEIGHTING : A > B > C > D > E > F > G > ...

■ BINARY PIXEL=1

☐ BINARY PIXEL=0

☐ BINARY PIXEL WITH MINIMUM DEVIATION OF NARIS=1

WEIGHTING : A > B > C > D > E > F > G > ...

✕ : EYE CENTROID 11

FIG. 7A
FIG. 7B
FIG. 7C
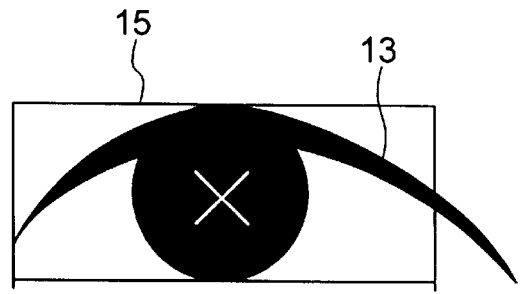
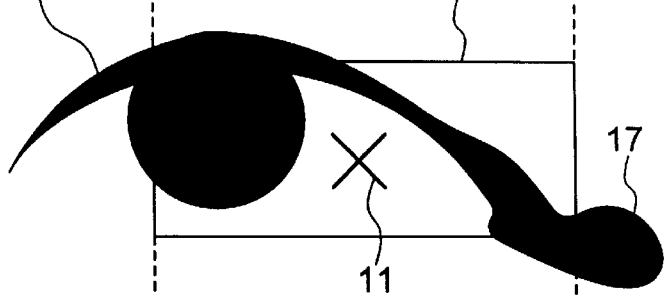
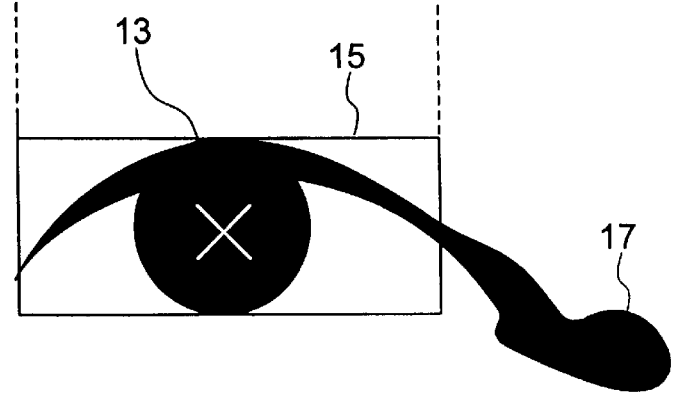
 : EYE CENTROID 11

■ BINARY PIXEL=1

☐ BINARY PIXEL=0

☐ BINARY PIXEL WITH MINIMUM DEVIATION OF NARIS=1

WEIGHTING : A > B > C > D > E > F > G > . . .

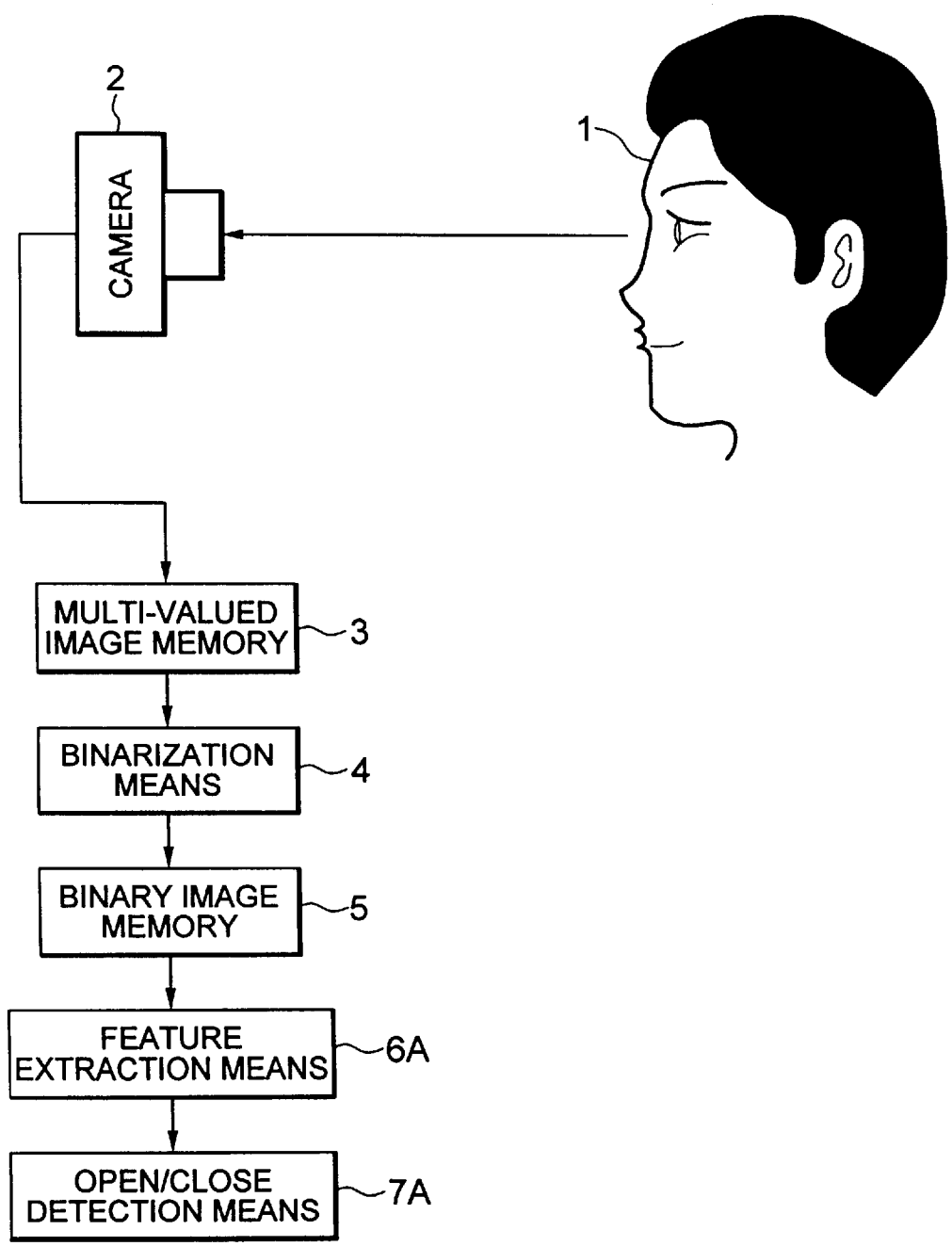

FACE IMAGE PROCESSING APPARATUS FOR EXTRACTION OF AN EYE IMAGE BASED ON THE POSITION OF THE NARIS

BACKGROUND OF THE INVENTION

1. Field of the Invention

The present invention relates to a face image processing apparatus for an eyewink detection, including extracting naris areas, which is relatively easy to be extracted, through image processing, then estimating the position of eyes based on the position of nares to extract eye areas, and detecting opening/closing states of the eyes from shape features of the eye areas.

2. Description of the Related Art

Conventional face image processing apparatuses include a face image processing apparatus described in Japanese Patent Application Laid-Open No. Hei 8-300978, as an example. This face image processing apparatus is characterized by a binary image on which eye and naris areas are extracted and the opening and closing of the eyes are detected.

FIG. 9 is a schematic structural view showing the face image processing apparatus described in Japanese Patent Application Laid-Open No. Hei 8-300978.

In this figure, a multi-valued image captured by a camera 2 serving as image input means for photographing the person to be detected 1 is temporarily stored in a multi-valued image memory 3 serving as multi-valued image storage means. The stored image is then converted into a binary image by binarization means 4, which is then temporarily stored in a binary image memory 5 serving as binary image storage means. Feature extraction means 6 extracts binary areas of the eyes and nares, and open/close detection means 7 detects opening/closing states of the eyes based on the shape feature of the eyes.

The operation will now be described with reference to FIGS. 10 to 12.

FIG. 10 is a flow chart showing an eye tracing algorithm in the face image processing apparatus shown in FIG. 9.

Referring to FIG. 10, a multi-valued image of the person to be detected 1 is obtained by the camera 2 photographing a face image (Step S1). A process of camera control is also involved herein. The multi-valued image obtained at Step S1 is temporarily stored frame by frame in the multi-valued image memory 3 at Step S2. The multi-valued image obtained at Step S2 is converted into a binary image by the binarization means 4 (Step S3), and is then temporarily stored frame by frame in the binary image memory 5 (Step S4).

Then, the feature extraction means 6 extracts nares out of the binary image outputted from the binary image memory 5 (Step S5), and both eye areas are estimated from configuration conditions of the face based on the position of nares, to set eye candidate areas (Step S6). Subsequently, at Step S7, eye areas are selected from the eye candidate areas; provided, however, that the shape feature or the deviation in the position on the previous screen is used to select the eye candidate areas. Subsequent to the initial extraction, positional estimations for both the eyes and the nares are carried out using the position on the previous screen as reference. Typically, the position of eyes is extracted using the position of nares as reference, but the case where nares have not been extracted will permit a complement with the position of eyes. If the eye binary area is selected at Step S7, the open/close detection means 7 detects open/close (Step S8), back to Step S1.

FIG. 11 is an example of error extraction of eyebrows when the eye binary area is selected at Step S7 as described above. Some of the eye binary area may often be lost in this way due to the illumination condition for the person to be detected or when a binarization threshold is much larger than the proper value. If eyes and eyebrows are involved in the eye candidate binary areas 16, an eyebrow similar in shape may be erroneously extracted. In addition, once an eyebrow is erroneously extracted, an inaccurate trace occurs because the relative position of the eye binary area to the naris binary area 12 is similar to the relative position of the eyebrow to the eye. This results in a difficult return to an accurate eye trace.

As opposed to FIG. 11, if the binarization threshold is lower than the proper value, the shaded outer canthus of the left eye may be involved in the eye binary area (see, FIG. 7(b)). The open/close detection means 7 provides an open/close detecting eye cut area 15 which is set using an eye centroid 11 as reference. Therefore, if there is any undesired binary area involved, the eye cut area will be set deviating from the actual eye area, and no correct open/close detection can be carried out.

FIG. 12 is a flow chart showing a specific operation for the open/close detection at Step S8 in FIG. 10.

A centroid position is set at Step S10 in the eye binary area selected at Step S7. At Step S11, an eye area is cut for the open/close detection so that the right-hand and left-hand portions in the horizontal direction of the face may be balanced using the eye centroid as reference. At Step S12, the shape feature of the outer canthus is extracted on the eye binary area within the open/close detecting eye cut area, regarded as an eye evaluation functional value. At Step S13, the eye evaluation functional value is compared to an open/close threshold, leading to an eye opening detection at Step S14 or an eye closure detection at Step S15 in accordance with the result. When the eye closure detection is resulted, the time period of closing the eye is counted at Step S16.

Alternatively, conventional face image processing apparatuses using a template include a face image processing apparatus described in Japanese Patent Application Laid-Open No. Hei 8-175218, for instance. This face image processing apparatus is characterized by including template production means for producing an objective template for the person to be detected, in which a preset standard face template is successively vertically and horizontally moved across a picked-up image to perform a correlative operation, and eye area detection means for detecting an eye area of the person to be detected using such an objective template.

FIG. 13 is a schematic structural view showing the face image processing apparatus described in Japanese Patent Application Laid-Open No. Hei 8-175218.

Referring to FIG. 13, an image processor 31 is connected to a camera 2 for photographing the person to be detected 1, and a face image of the person to be detected 1 is then delivered to the image processor 31. The image processor 31 incorporates an A/D converter, a normalization circuit, and a correlative operation circuit, in which an input image signal is converted into a digital signal to be then normalized for a light and shade image. A memory 32 is also connected to the image processor 31. A standard template and configuration data of the face elements such as eyes and eyebrows are in advance stored in the memory 32. The image processor 31 is further connected to an ECU (Electronic Control Unit) 33 and delivers the processing results to the ECU 33. The ECU 33 is so arranged as to determine the operation state of the person to be detected 1 from the processing results and to output a control signal to an alarm 34 to thereby issue an alarm.

However, there were problems as below with the conventional face image processing apparatus previously described in Japanese Patent Application Laid-Open No. Hei 8-300978.

Namely, binarization means converts a multi-valued image into a binary image for the image processing. In this case, gray information in the multi-valued image is eliminated. For this reason, the binarization threshold must be controlled every screen in accordance with the brightness of the face image of the person to be detected who was photographed, in order to correctly recognize the shape feature of the eyes/nares. The extraction results of the feature is greatly varied depend upon this binarization threshold.

Further, the binary shape feature unstably varies due to influence of the binarization threshold. For example, the entire portion of the face may vary in brightness or the face orientation may be changed during the transition from the naris extraction to the eye extraction. Further, the binarization threshold may be suitable for the naris extraction while the binarization threshold may not be suitable for the eye extraction because different brightness is given to some parts of the face. In the foregoing cases, the shape of eyes and nares cannot be correctly extracted for the binary area at the same time, from the binary image generated with a unique binarization threshold for every screen. In particular, if the eye binary area is broken in shape, the eyebrow might be erroneously extracted, or the open/close detection might not be correctly carried out even with a correct eye extraction.

In other words, some of the eye binary area may often be lost in this way due to the illumination condition for the person to be detected or when a binarization threshold is much larger than the proper value. If eyes and eyebrows are involved in the eye candidate binary areas, an eyebrow similar in shape may be erroneously extracted. In addition, once an eyebrow is erroneously extracted, an inaccurate trace occurs because the relative position of the eye binary area to the naris binary area is similar to the relative position of the eyebrow to the eye. This results in a difficult return to an accurate eye trace, and such a problem may occur.

In addition, open/close detection means provides an open/close detecting eye cut area which is set using an eye centroid as reference. Therefore, if there is any undesired binary area involved, the area will be set deviating from the actual eye area, and no correct open/close detection can be carried out. Such a problem may also occur.

On the other hand, in the conventional face image processing apparatus described in Japanese Patent Application Laid-Open No. Hei 8-175218, a positional relation in the vertical direction between eyes and eyebrows is invariable even with the vertical movement of the face. Therefore, the eye area can ensure to be specified such that an objective eye vicinity area is used to detect an eye vicinity area, where the upper black portion is an eyebrow and the lower black portion is an eye. However, difficulty arises in that, taking the movement of the face into consideration, the image must be scanned to a broad extent for a template matching, resulting in increasing the time period of processing the correlative operation.

SUMMARY OF THE INVENTION

The present invention has been therefore made to overcome the foregoing problems, and therefore has an object of the present invention is to provide a face image processing apparatus capable of preventing the error extraction of the eye when extracted, improving reliability of the open/close detection through a two-dimensional feature of the eye area, and also quickly performing the open/close detection.

According to a first aspect of the present invention, there is provided a face image processing apparatus comprising: image input means for inputting a face image of a person to be detected; multi-valued image storage means for temporarily storing the light and shade image obtained by said image input means; binarization means for binarizing the light and shade image outputted from said multi-valued image storage means; binary image storage means for temporarily storing the binary image obtained by said binarization means; feature extraction means for extracting a naris area from said binary image outputted from said binary image storage means, and for extracting an eye area based on the naris area; and open/close detection means for detecting the opening/closing states of the eye based on the shape feature of the eye area obtained by said feature extraction means.

According to this arrangement, such an effect may be obtained that the opening/closing states of the eyes can be correctly detected, resulting in improving reliability in the open/close detection, and the open/close detection can be performed in a short processing time since a template matching is not required as opposed to the conventional one.

According to a second aspect of the present invention, in a face image processing apparatus of the first aspect of the present invention, said feature extraction means comprises: naris area extraction means for extracting a naris binary area from the binary image outputted from said binary image storage means; and eye area extraction means for extracting an eye binary area using as reference the naris binary area extracted by said naris area extraction means from the binary image outputted from said binary image storage means.

According to this arrangement, there can be obtained an effect that the opening/closing states of the eye can be more correctly detected.

According to a third aspect of the present invention, in a face image processing apparatus of the second aspect of the present invention, said eye area extraction means uses as a weight of eye candidate pixels at the eye extraction a deviation in distance between the naris binary area extracted by said naris area extraction means and the eye binary area at the previous extraction of the eye.

According to this arrangement, the effect thereof is such that the eye area can be correctly extracted with substantially an increased credibility of the eye candidate pixels, inhibiting the error extraction.

According to a fourth aspect of the present invention, in a face image processing apparatus of any one of the first to third aspects of the present invention, said open/close detection means uses eye area pixels weighted through the deviation of the naris when the centroid position of the eye is set as reference of cutting the eye area for the open/close detection.

According to this arrangement, such an effect can be obtained that the opening/closing states of the eye can be more correctly detected.

BRIEF DESCRIPTION OF THE DRAWINGS

In the accompanying drawings, wherein:

FIGS. 7(a) to 7(c) are illustrations showing the open/close detecting eye cut area and the eye centroid when the shaded outer canthus is involved in the eye binary area;

FIG. 9 is a structural view showing a conventional face image processing apparatus;

DETAILED DESCRIPTION OP THE PREFERRED EMBODIMENT

A preferred embodiment of the present invention will now be described with reference to the drawings.
Embodiment 1

Figure 1:
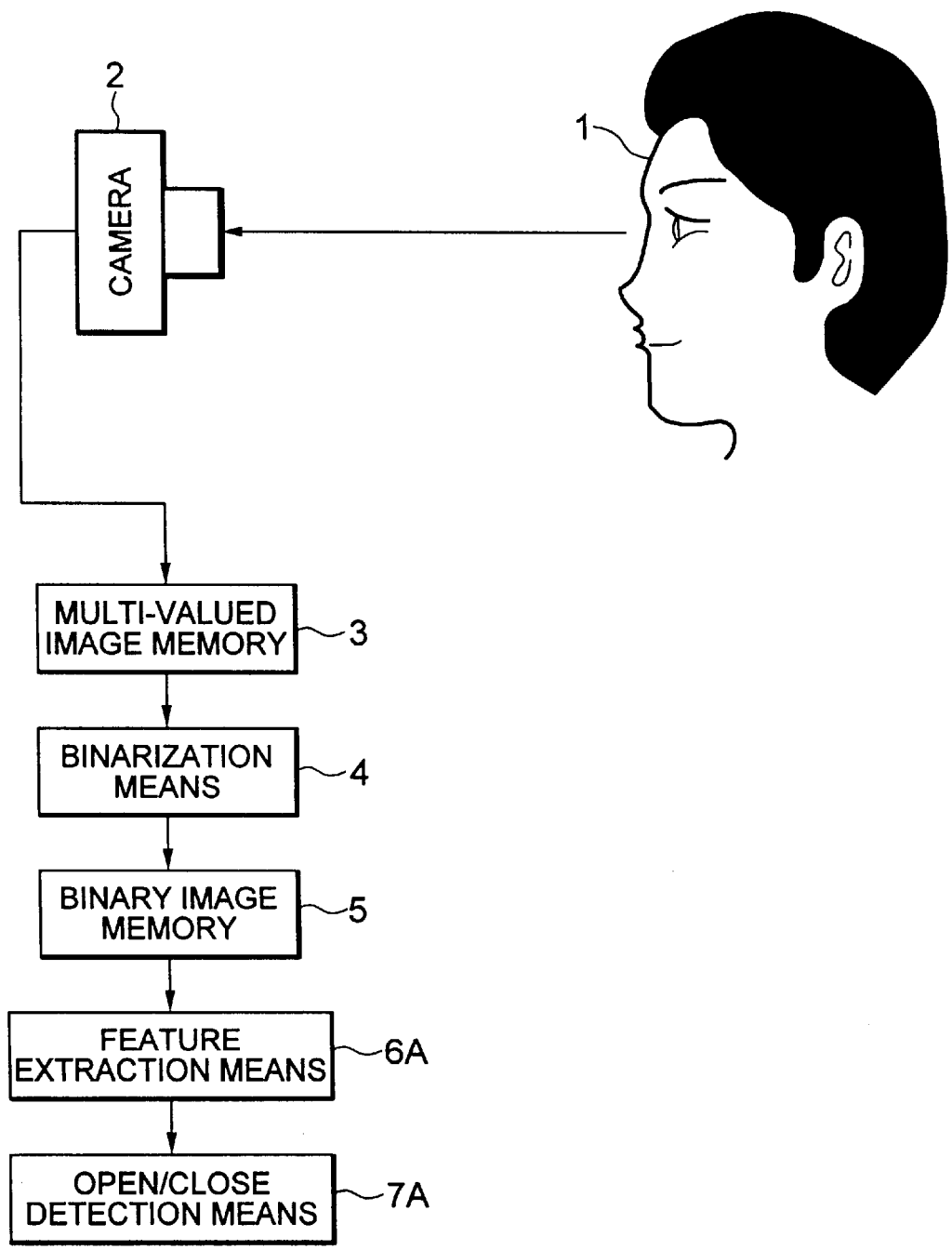
FIG. 1 is a structural view showing Embodiment 1 of the present invention.

FIG. 1 is a structural view showing Embodiment 1 of the present invention. It is noted that in FIG. 1, the same reference numerals are designated to corresponding parts to those of FIG. 9 for omission of the overlapped explanation.

Referring to FIG. 1, feature extraction means 6A extracts eye/naris binary areas, and open/close detection means 7A then detects the open/close states of the eye based on the shape feature of the eye. The feature extraction means 6A and the open/close detection means 7A are both implemented as software by a microcomputer or the like. This very part of algorithm is different from that of conventional ones. The feature extraction means 6A includes naris area extraction means for extracting a naris binary area from a binary image outputted from the binary image memory 5, and eye area extraction means for extracting an eye binary area using as reference the naris binary area extracted by the naris area extraction means from the binary image outputted from the binary image memory 5.

The operation will now be described with reference to FIGS. 2 to 8.

Figure 2:
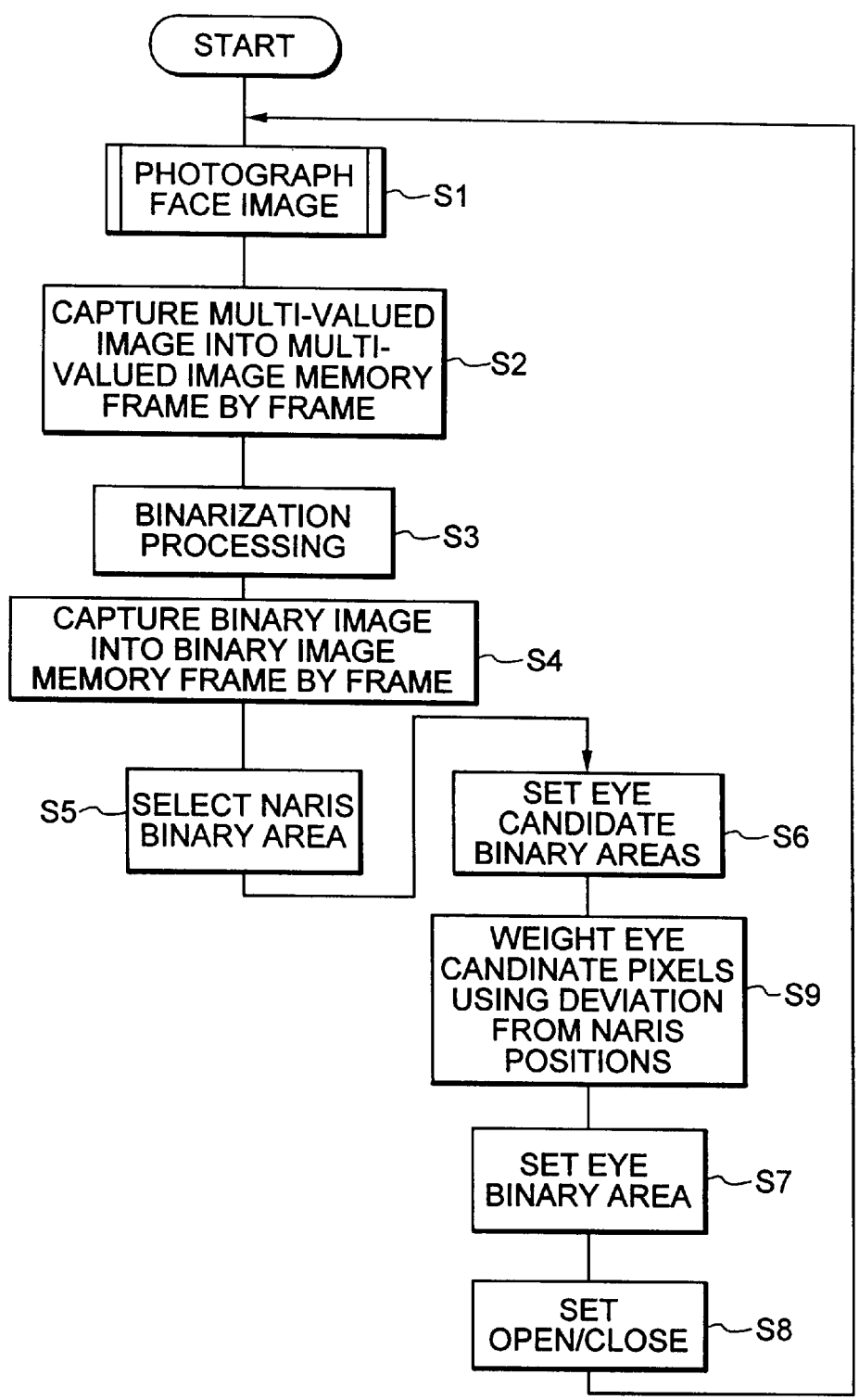
FIG. 2 is a flow chart showing an eye/naris tracing algorithm in accordance with Embodiment 1 of the present invention.

FIG. 2 is a flow chart showing an eye tracing algorithm in accordance with Embodiment 1 of the present invention.

As opposed to the conventional example, pixels constituting eye candidate areas are weighted for an eye area selection from the eye candidate areas at Step S9, using the deviation in the distance at the previous extraction of the eye between the position of eyes and nares. Thus, the eye area can be selected with substantially an increased credibility of the respective eye candidate areas. The weighted pixels are also used to determine the centroid position of the eye within the eye binary area during the open/close detection process at Step S8.

A description will now be given of a flow chart of FIG. 2.

The following steps are carried out in the same manner as those of the conventional one, and the explanation thereof will be omitted: photographing a face image (Step S1); capturing a multi-valued image into a multi-valued image memory (Step S2); binarization processing (Step S3); capturing a binary image into a binary image memory (Step S4); selecting a naris binary area (Step S5); setting eye candidate binary areas (Step S6); and selecting the eye binary area (Step S7).

For the eye candidate binary areas set at Step S6, the pixels constituting the eye candidate binary areas are weighted at Step S9 using the deviation in distance between the position of nares and the position of eyes when previously extracted.

Figure 3:
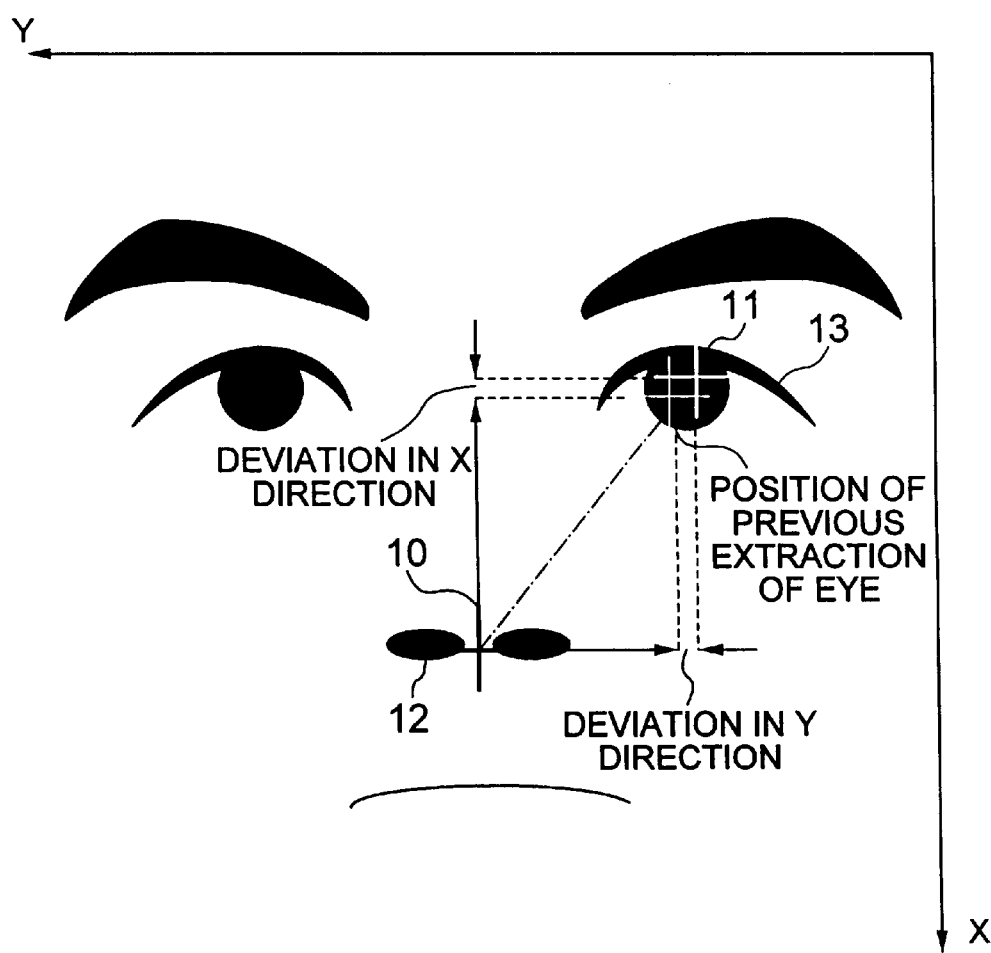
FIG. 3 is an illustration showing deviations in distance between a naris centroid and an eye centroid on a binary image of the person to be detected.

FIG. 3 depicts the deviations in distance on the face binary image between the naris centroid 10 and the eye centroid 11 at the previous extraction.

Figure 4A:
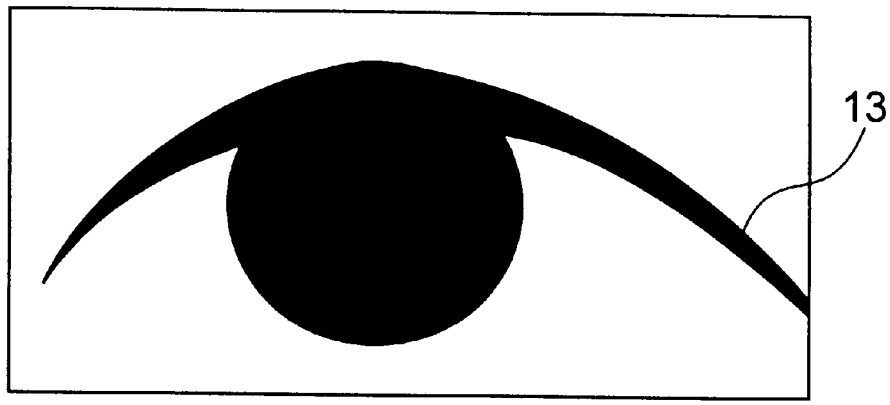
FIGS. 4(a) and 4(b) are illustrations showing an example in which eye candidate binary pixels are weighted in accordance with Embodiment 1 of the present invention.
Figure 4B:
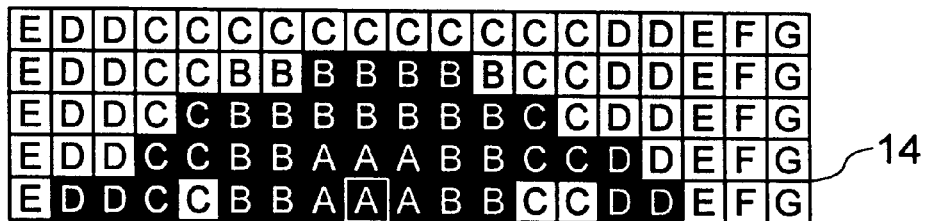

FIGS. 4(a) and 4(b) depict how the pixels are weighted using the distance from the eye to the naris, as shown in FIG. 3. FIG. 4(b) depicts that every pixel is weighted to the eye binary area 13 shown in FIG. 4(a), based on the distance from the previous extraction of the eye to the naris. It is assumed that the minimum distance from the eye to the naris provides the maximum weight, with the weight descending in the order of A>B>C>. . . .

As shown in FIG. 4(b), the eye binary area 13 is selected, based on the shape feature and the weight, from the eye candidate areas 14 that have been weighted. It is also assumed that the centroid position of the selected eye binary area 13 be obtained through the weighted pixels.

Figures 5A, 5B:
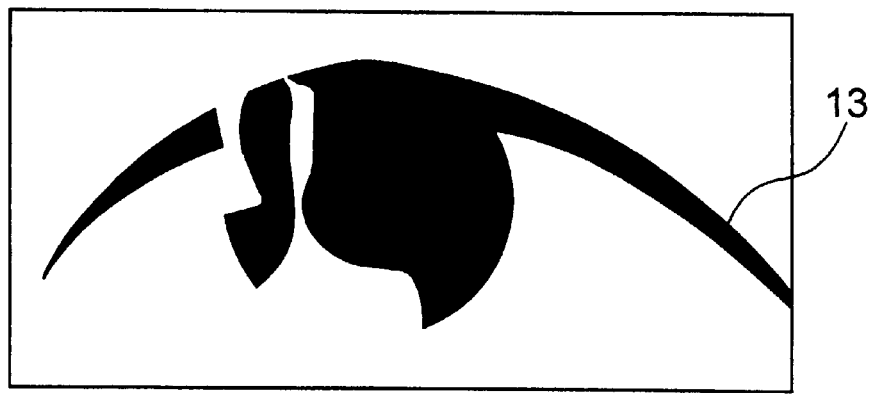
FIGS. 5(a) and 5(b) are illustrations showing an example in which the eye candidate binary pixels are weighted in accordance with Embodiment 1 of the present invention in the case where some of the eye binary area is lost.
Figure 11:
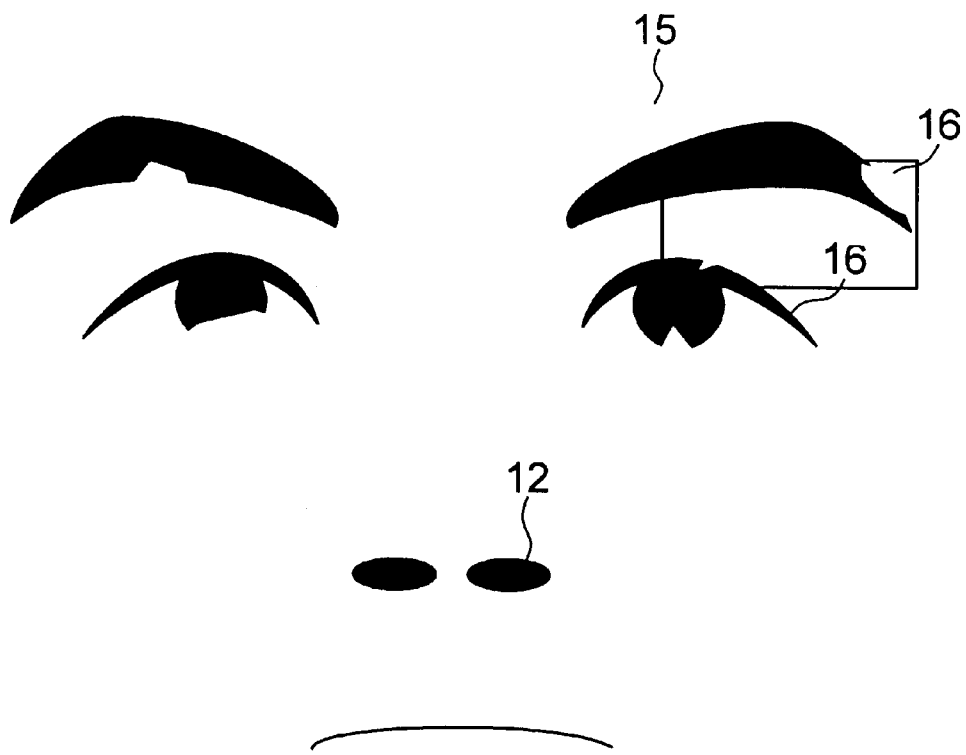
FIG. 11 is an illustration showing an example of error extraction of eyebrows when the eye is extracted.
Figure 12:
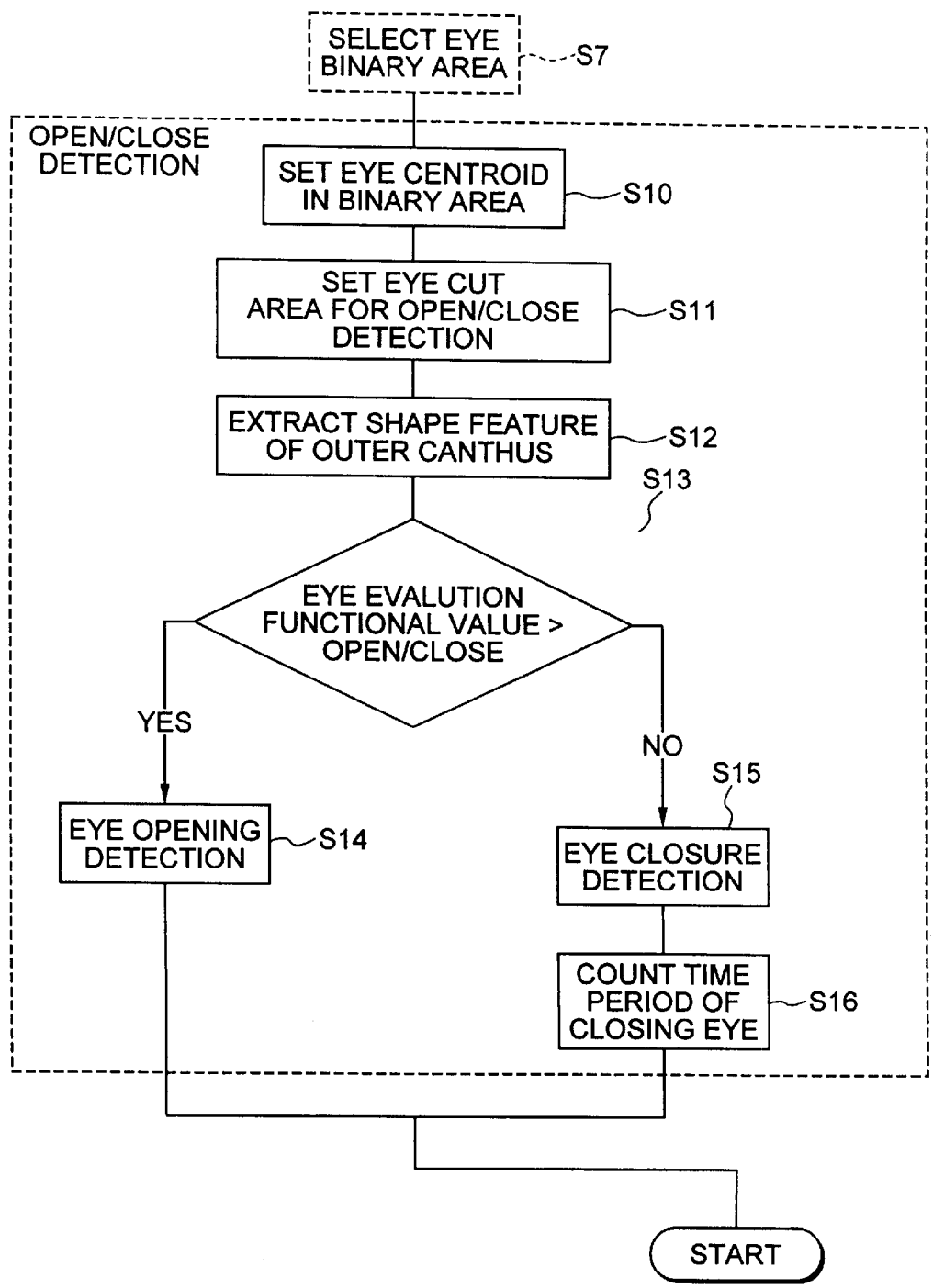
FIG. 12 is a flow chart showing a conventional algorithm for the open/close detection.
Figure 13:
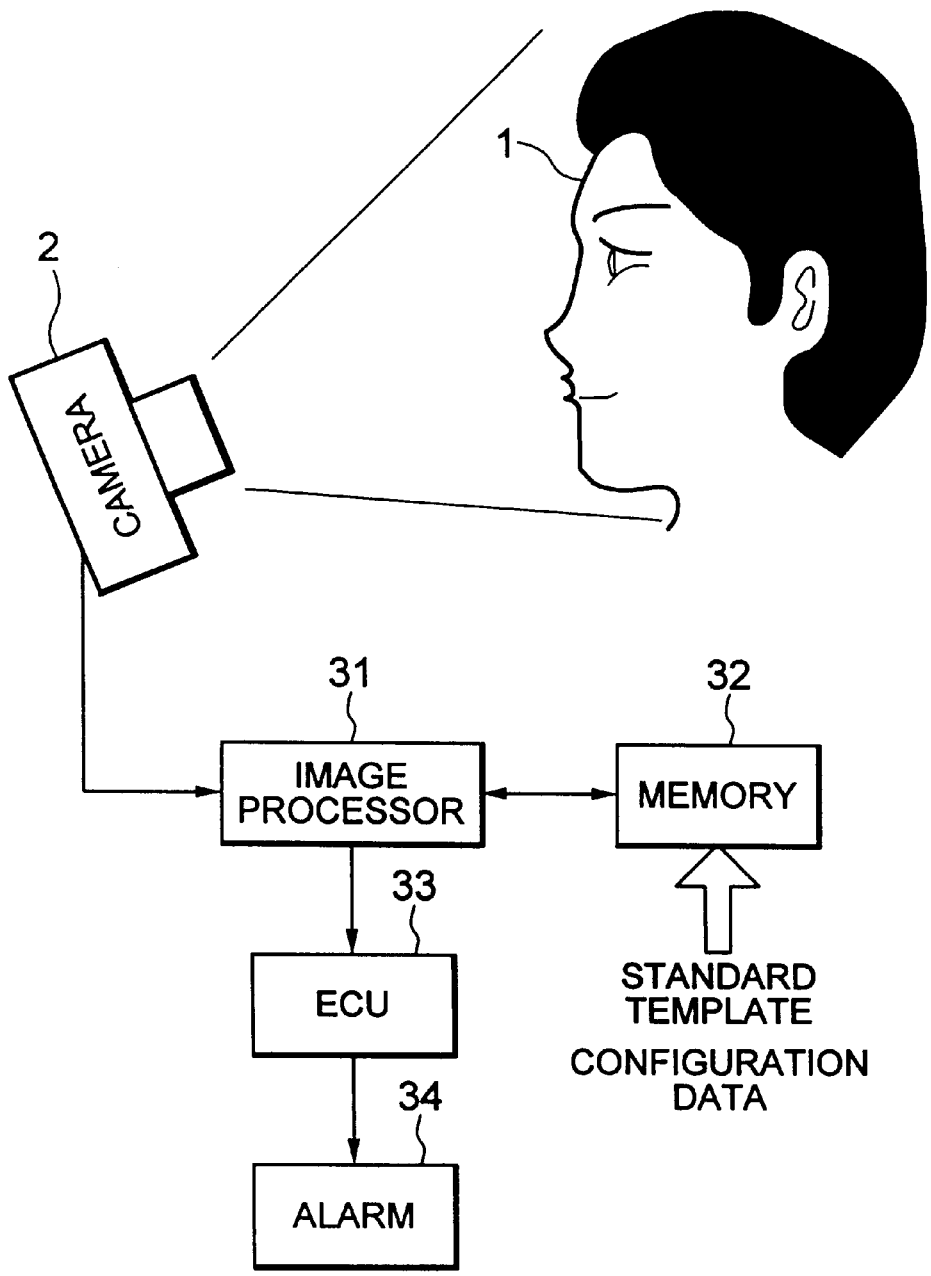
FIG. 13 is a structural view showing a conventional face image processing apparatus using a template matching.

FIGS. 5(a) and 5(b) depict that the pixels are weighted on the eye binary area of FIG. 11, using the distance from the eye binary area to the naris. The positional relation of the eye binary area relative to the position of the naris which is used as a reference position, can be reflected in the eye extraction algorithm on a pixel-by-pixel basis. Therefore, should the eye area be broken in shape or should the number of the pixels be small, the eye could be increasingly credible, inhibiting such an error extraction as shown in FIG. 11.

Figures 6A, 6B:
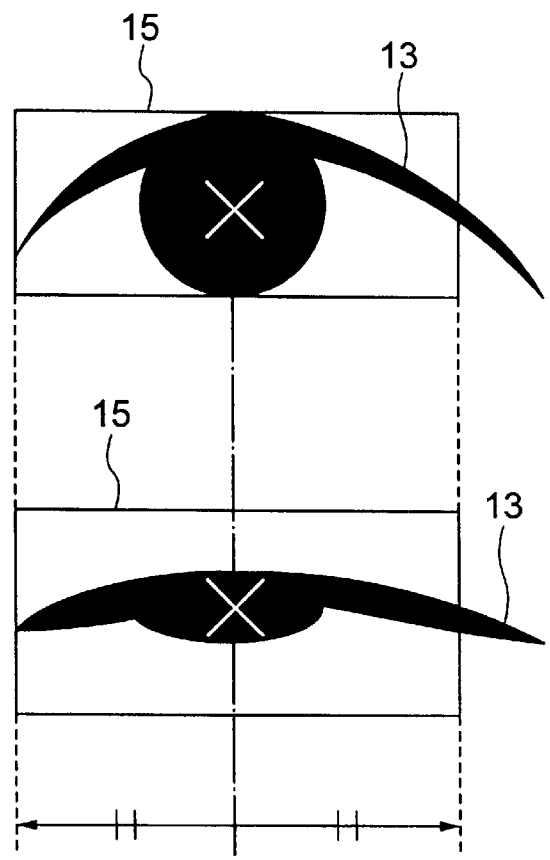
FIGS. 6(a) and 6(b) are illustrations showing how the eye binary area changes in shape and showing an open/close detecting eye cut area when the eye is open and closed.

FIGS. 6(a) and 6(b) depict an open/close detecting eye cut area 15 within the binary area 13 selected as an eye area. A certain range of the eye binary area 13 is cut as the open/close detecting eye cut area 15 so that the right-hand and left-hand portions in the horizontal direction of the face may be balanced about the eye centroid 11. FIG. 6(a) depicts the opening state of eye and FIG. 6(b) depicts the closing state of eye. The opening/closing states of eye can be detected while attention is drawn to the change in the shape feature, such as an inclination of the outer canthus, of the eye binary area within the open/close detecting eye cut area 15.

FIG. 7(a) depicts the eye centroid 11 relative to the eye binary area 13 and the open/close detecting eye cut area 15. FIGS. 7(b) and 7(c) depict the eye binary area that is binarized involving the shaded outer canthus, and more specifically, FIG. 7(b) depicts the eye centroid obtained without the weight being based on the distance from the eye binary area to the naris, and FIG. 7(c) depicts the eye centroid obtained with the weight being based on the distance from the eye binary area to the naris.

In FIG. 7(b), the eye binary area 13 involves a shaded outer canthus binary area 17, and the centroid position of the eye 11 is set deviating from the actual centroid position of the eye. Therefore, the open/close detecting eye cut area 15 will be set in position close to the outer canthus, and there is a fear that the open/close detection using the shape feature be incorrectly carried out.

Figure 8A:
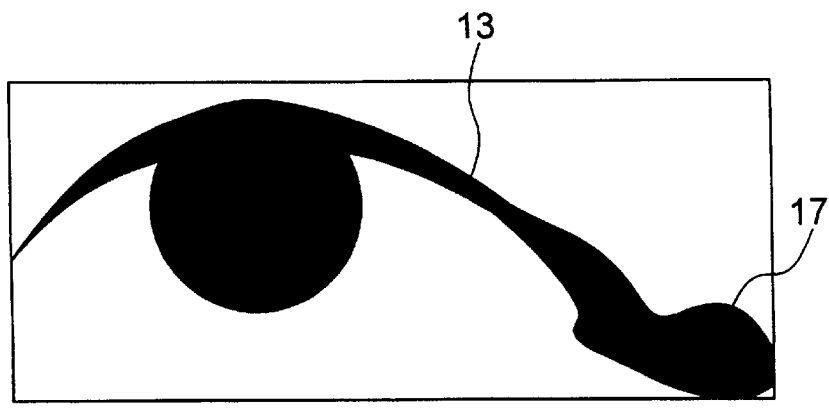
FIGS. 8(a) and 8(b) are illustrations showing an example in which the eye candidate binary pixels are weighted in accordance with Embodiment 1 of the present invention when the shaded outer canthus is involved in the eye binary area.
Figure 8B:
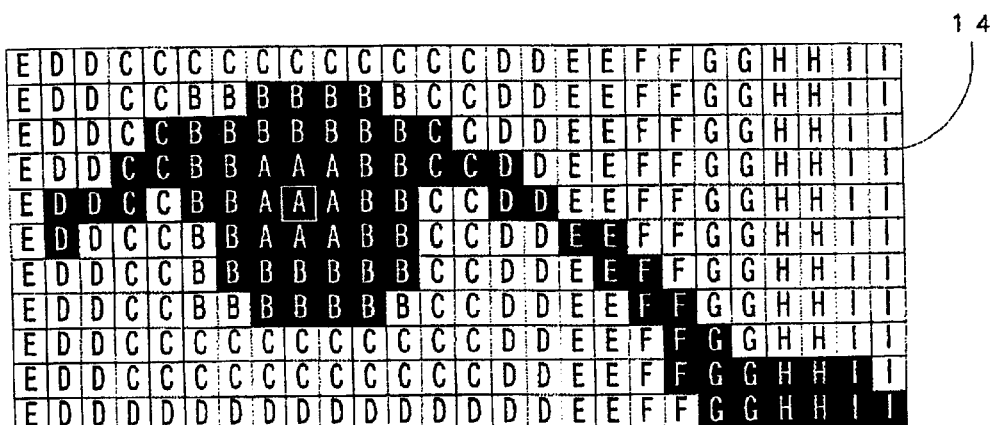
Figure 10:
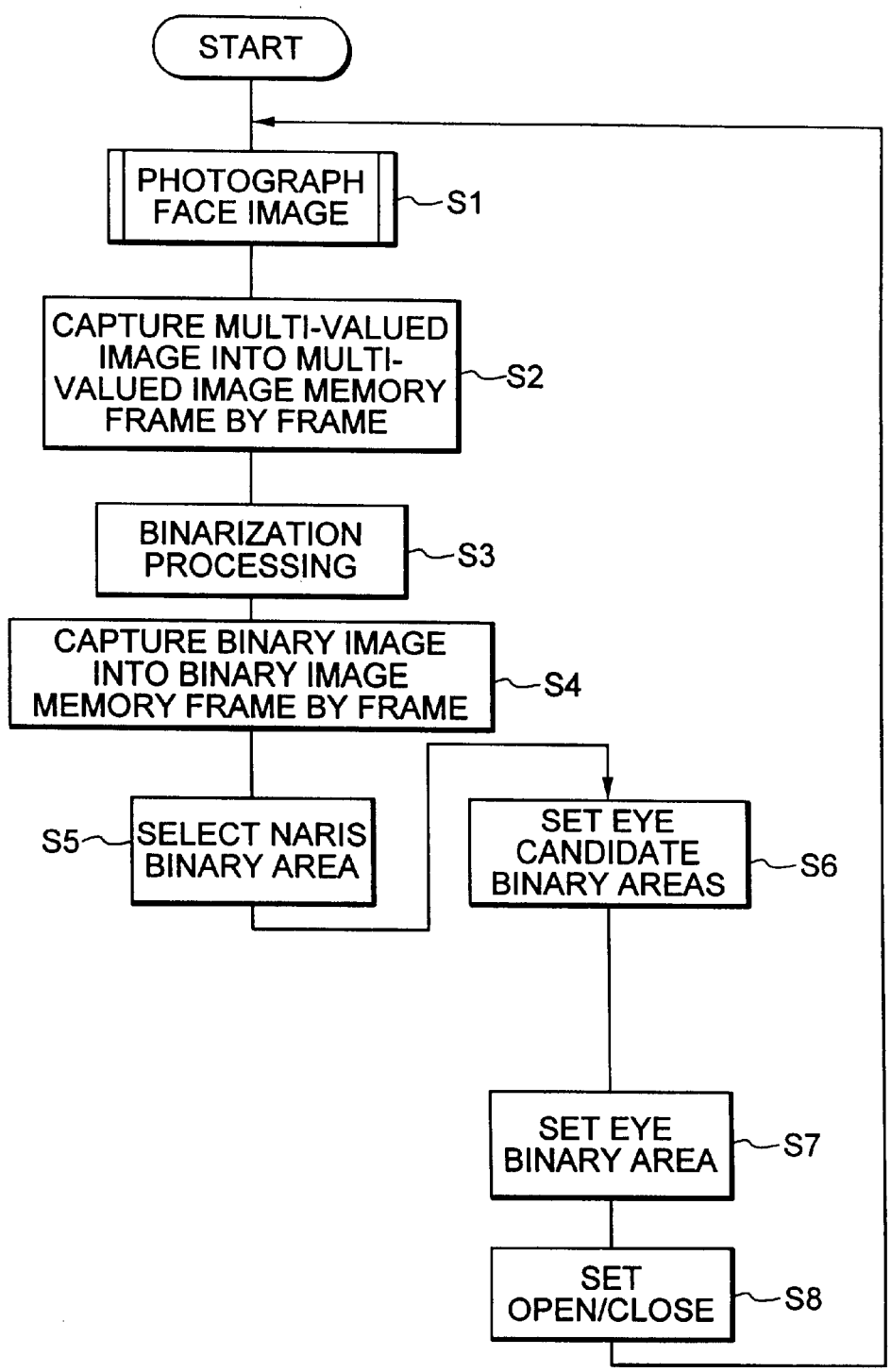
FIG. 10 is a flow chart showing an eye/naris tracing algorithm in the conventional face image processing apparatus.

In FIG. 7(c), the pixels constituting the shaded outer canthus binary area 17 are weighted in a lower position based on the distance from the eye centroid to the naris as shown in FIG. 8. Thus, the weighted pixels allow the eye centroid 11 to be set in the actual position of the eye. Therefore, the open/close detecting eye cut area 15 can be properly set, making it possible to correctly detect the opening/closing states.

While the embodiment of the present invention employs weighted pixels for the binary image, the same effect may also be expectable to a multi-valued image.

What is claimed is:

1. A face image processing apparatus comprising:

image input means for inputting a face image of a person to be detected;

multi-valued image storage means for temporarily storing the light and shade image obtained by said image input means;

binarization means for binarizing the light and shade image outputted from said multi-valued image storage means;

binary image storage means for temporarily storing the binary image obtained by said binarization means;

feature extraction means for extracting a naris area from said binary image outputted from said binary image storage means, and for extracting an eye area based on the naris area; and open/close detection means for detecting the opening/closing states of the eye based on the shape feature of the eye area obtained by said feature extraction means, wherein said feature extraction means comprises: naris area extraction means for extracting a naris binary area from the binary image outputted from said binary image storage means; and eye area extraction means for extracting an eye binary area using as reference the naris binary area extracted by said naris area extraction means from the binary image outputted from said binary image storage means, and wherein said eye area extraction means uses as a weight of eye candidate pixels at the eye extraction a distance between the naris binary area extracted by said naris area extraction means and the eye binary area at the previous extraction of the eye.

2. A face image processing apparatus comprising:

image input means for inputting a face image of a person to be detected;

multi-valued image storage means for temporarily storing the light and shade image obtained by said image input means;

binarization means for binarizing the light and shade image outputted from said multi-valued image storage means;

binary image storage means for temporarily storing the binary image obtained by said binarization means;

feature extraction means for extracting a naris area from said binary image outputted from said binary image storage means, and for extracting an eye area based on the naris area; and open/close detection means for detecting the opening/closing states of the eye based on the shape feature of the eye area obtained by said feature extraction means, wherein said open/close detection means uses eye area pixels weighted based on the distance from the eye area to the naris area, when the centroid position of the eye is set as reference of cutting the eye area for the open/close detection.

* * * * *